(12) United States Patent
Stoutenburgh et al.

(10) Patent No.: US 9,492,127 B2
(45) Date of Patent: Nov. 15, 2016

(54) RADIOLOGICAL IMAGING DEVICE WITH ADJUSTABLE BED

(71) Applicant: Epica International, Inc., San Clemente, CA (US)

(72) Inventors: Gregory William Stoutenburgh, San Clemente, CA (US); Damiano Fortuna, Rignano Sull'Arno (IT); Luca Ferretti, Pisa (IT)

(73) Assignee: Epica International, Inc., San Clemente, CA (US)

( * ) Notice: Subject to any disclaimer, the term of this patent is extended or adjusted under 35 U.S.C. 154(b) by 131 days.

(21) Appl. No.: 14/603,951

(22) Filed: Jan. 23, 2015

(65) Prior Publication Data

US 2015/0208991 A1     Jul. 30, 2015

Related U.S. Application Data

(60) Provisional application No. 61/932,034, filed on Jan. 27, 2014, provisional application No. 61/944,956, filed on Feb. 26, 2014.

(51) Int. Cl.
| | |
|---|---|
| *A61B 6/04* | (2006.01) |
| *A61G 7/10* | (2006.01) |
| *A47C 13/00* | (2006.01) |
| *A61B 6/03* | (2006.01) |

(52) U.S. Cl.
CPC ............ *A61B 6/0407* (2013.01); *A61B 6/032* (2013.01); *A61B 6/0442* (2013.01); *A61B 6/0492* (2013.01)

(58) Field of Classification Search
USPC ......... 378/20, 204, 205, 206, 208, 209, 210; 250/370.08, 370.09, 363.05, 363.08, 250/363.01, 363.02, 453.11; 5/81.1 R, 5/81.1 HS, 136, 600, 601, 607, 608, 610, 5/611, 621–624
See application file for complete search history.

(56) References Cited

U.S. PATENT DOCUMENTS

| | | | |
|---|---|---|---|
| 4,426,726 A | 1/1984 | Cheetham | |
| 4,662,366 A * | 5/1987 | Tari | A61F 5/3723 128/877 |
| 6,073,291 A * | 6/2000 | Davis | A61B 6/0485 414/676 |
| 6,150,662 A | 11/2000 | Hug et al. | |
| 6,260,220 B1 | 7/2001 | Lamb et al. | |
| 6,728,979 B1 | 5/2004 | Robert | |
| 8,579,244 B2 * | 11/2013 | Bally | A61G 7/1025 248/224.7 |
| 2002/0130535 A1 | 9/2002 | Dick et al. | |
| 2012/0104276 A1 | 5/2012 | Miller et al. | |
| 2015/0208990 A1 * | 7/2015 | Stoutenburgh | A61B 6/0407 378/62 |
| 2016/0015343 A1 * | 1/2016 | Fortuna | A61B 6/4435 378/51 |
| 2016/0015344 A1 * | 1/2016 | Fortuna | A61B 6/4435 378/51 |

* cited by examiner

*Primary Examiner* — Bernard Souw
(74) *Attorney, Agent, or Firm* — Steptoe & Johnson LLP

(57) ABSTRACT

A radiological imaging system for obtaining images of at least a portion of the internal anatomy of a patient is disclosed. According to one embodiment, the radiological imaging system includes a bed including a support surface, pillars extending along an elongational axis of the bed, and pivots terminal ends of the pillars. The radiological imaging system further includes a load-bearing structure comprising a frame that supports the bed, and adjustable fasteners removably attached to the frame, wherein the adjustable fasters are threaded cylinders. The pivots are placed on the adjustable fasteners, and the threaded cylinders of the adjustable fasteners are rotated to adjust a positioning of the pivots, and the shape of the support surface.

33 Claims, 21 Drawing Sheets

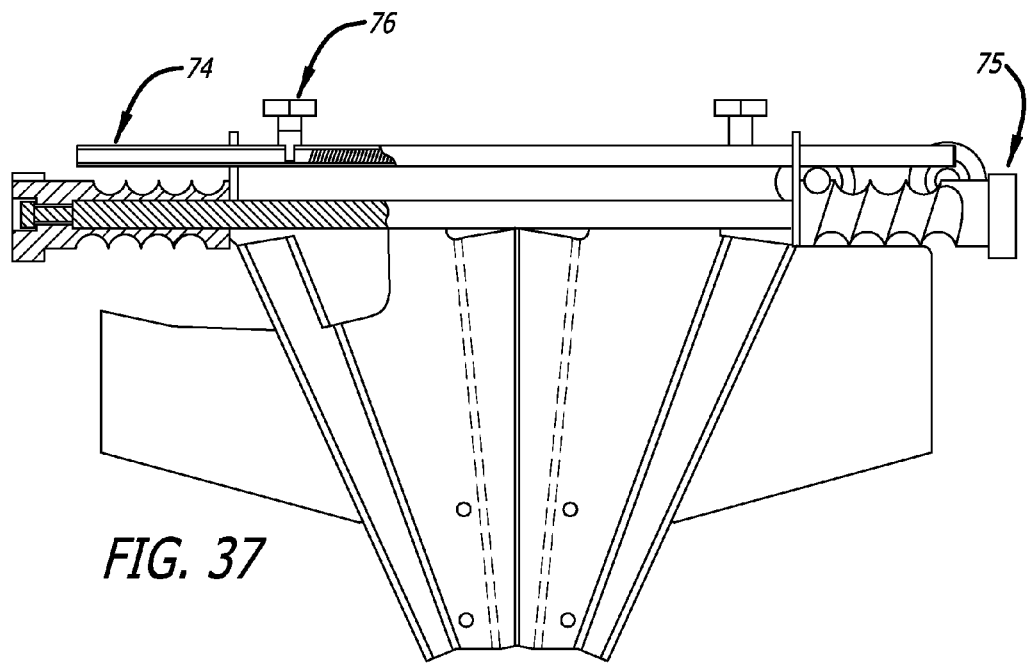
FIG. 37
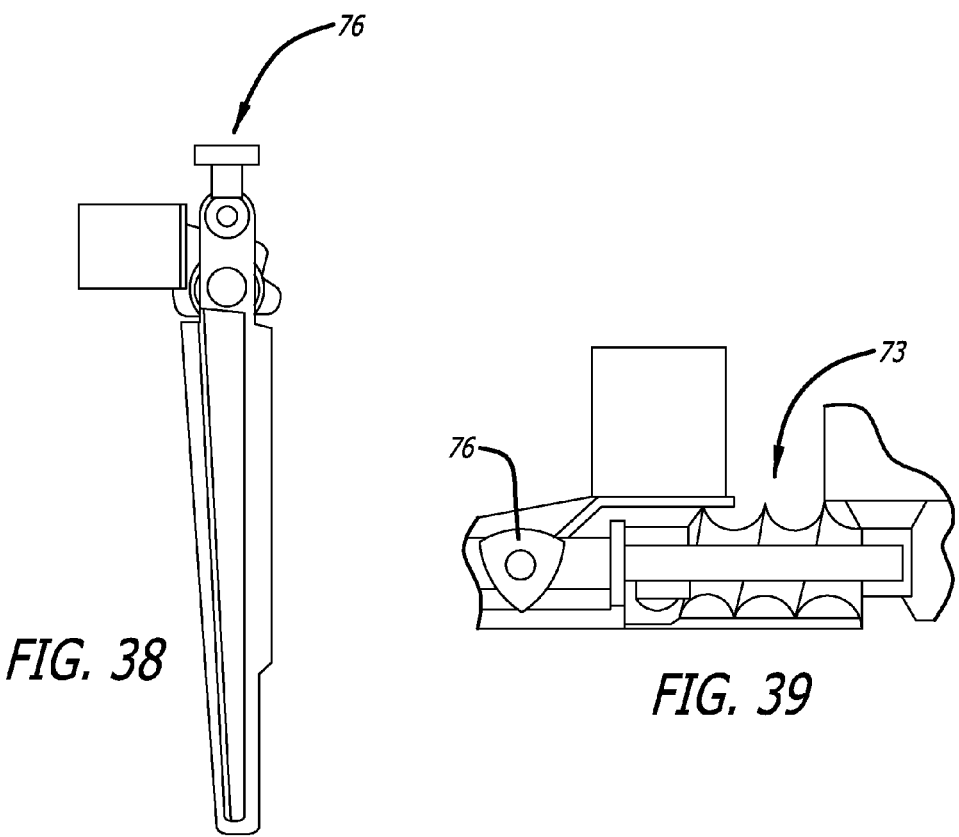
FIG. 38
FIG. 39

FIG. 41
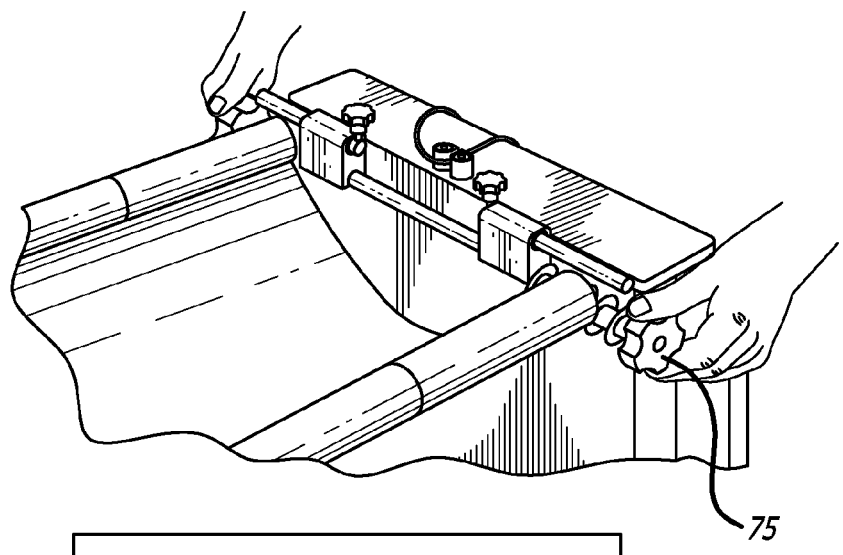
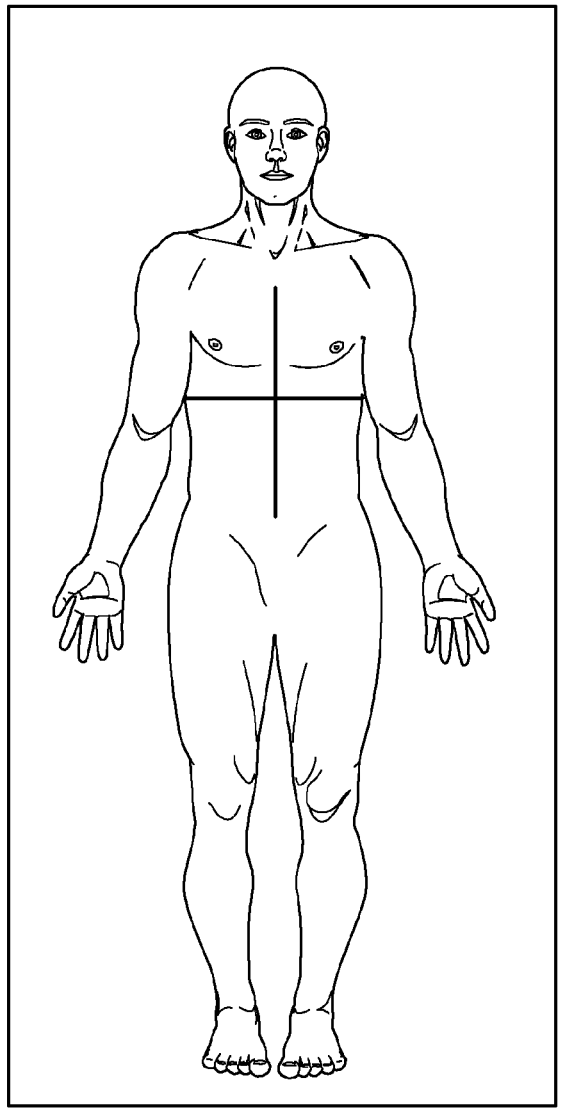

RADIOLOGICAL IMAGING DEVICE WITH ADJUSTABLE BED

CROSS-REFERENCE TO RELATED APPLICATIONS

The present application claims the benefit of and priority to U.S. Provisional Patent Application Ser. No. 61/932,034 filed on Jan. 27, 2014 and 61/944,956 filed on Feb. 26, 2014, which are hereby incorporated by reference.

This application is related to co-pending U.S. patent application Ser. No. 14/603,917, filed Jan. 23, 2015, entitled RADIOLOGICAL IMAGING SYSTEM, which is hereby incorporated by reference in their entirety.

FIELD

The present disclosure relates in general to the field of a radiological imaging system, and in particular, to a system and method for providing a radiological imaging system including an adjustable bed.

BACKGROUND

Radiological imaging devices currently available on the market have a standard structure including a flat bed on which a patient is placed in order to perform image scanning of the patient. To keep the patient still during the image scanning and thereby ensure the expected performance of the radiological imaging procedure, the bed is typically fitted with straps to restrain the patient. However, the straps may prevent the passage of the X-rays and thereby the correct visualization of the portions adjacent to the straps.

For this reason, in some imaging procedures, the straps covering a portion of the area of interest are practically unusable, and the patient may be required to stay still or held by the operator, who is therefore exposed to the X-rays. Additionally, the radiological imaging device may require a specific detector for each analysis and can perform only one type of analysis at a time.

As a result, in the case in which a patient needs to undergo several analyses, the patient needs to be taken from the radiological imaging device, placed on a bed, moved, picked up again and then laid on a second radiological imaging device. Such maneuvers often entail problems for the patient and the procedure, and therefore need to be performed with particular care and expertise. Consequently, the length of time needed to perform the aforementioned manoeuvres increases.

Additionally, a patient may need to be repositioned for optimal imaging, but the bed of existing imaging devices does not allow easy maneuver of patients, especially when the patient is secured to the bed by straps or restraints. Consequently, the length of time needed to perform the aforementioned maneuvers increases.

SUMMARY

Existing limitations associated with the foregoing, as well as other limitations, can be overcome by a system, method, and a bed for use with a radiological imaging device. Although the bed is described in relation to a radiological imaging device, the bed may be used with other devices or simply to transport a patient.

Briefly, and in general terms, the present disclosure is directed to various embodiments of a radiological imaging system. The radiological imaging system is used to obtain images of at least a portion of the internal anatomy of a patient and permits the patient to be moved simply and quickly, and reduces risks to the patient. According to one embodiment, the radiological imaging system includes a bed including a support surface, pillars extending along an elongational axis of the bed, and pivots attached to terminal ends of the pillars. The radiological imaging system further includes a load-bearing structure having a frame to support the bed. The radiological imaging system also includes adjustable fasteners removably attached to the frame. The adjustable fasteners may be threaded cylinders in one embodiment. In other embodiments, the adjustable fasteners may be any type of fastener. In one embodiment, the pivots are placed on the adjustable fasteners, and the threaded cylinders of the adjustable fasteners are rotated to adjust a positioning of the pivots, and the shape of the support surface.

In one embodiment, the bed is a flexible bed, and the support surface is a flexible support surface. The flexible bed may be made of carbon fiber. In another embodiment, the support surface is a rigid surface having a flat, semi-circular or triangular profile shape. In some embodiments, the support surface is made of a radio-transparent material.

In one embodiment, the frame includes a front frame, a rear frame, a front support panel attached to the front frame, and a real support panel attached to the rear frame. The adjustable fasteners may be arranged along a width of the front support panel and the rear support panel. The front support panel and the rear support panel may further include at least one anchor for securing and adjusting supporting ropes. Also, the front support panel and the rear support panel may include at least one shaft hole that provides a passage for supporting the supporting ropes. In one embodiment, the system may include a height adjustment control disposed on the front support panel and the rear support panel for adjusting a height of the bed. The adjustable fasteners may be fastened to the frame using a fastener control knob that is disposed on the frame.

According to one embodiment, the radiological imaging system further includes a gantry and a translation mechanism to move the gantry in a sliding direction that extends along the elongational axis of the bed. The translation mechanism may include a linear guide and a carriage that control a translational position of the gantry with respect to the bed. In some embodiments, the linear guide is motorized.

In one embodiment, the pivots are secured to the adjustable fasteners using a lock. The lock may be a spring-loaded lock or any other type of lock, such as a cam lock. In one embodiment, the threaded cylinders of the adjustable fasteners are exposed when the lock is in a disengaged position. The lock may extend a portion of the threaded cylinders in an engaged position.

In one embodiment, the radiological imaging system may include a laser centering system that projects a visual marker on a patient placed on the bed. The radiological imaging system may also include a source suitable to emit radiation, and a detector suitable to receive the radiation that traversed a portion of a patient positioned on the bed.

This disclosure is also directed to a bed for use with a radiological imaging system. In one embodiment, the bed includes a frame and pillars extending along an elongational axis of the bed that is connected to the frame. A support surface of the bed is connected to the pillars. In some embodiments, the bed further includes adjustable fasteners removably attached to the frame. The adjustable fasteners may be threaded cylinders or any other type of fastener. The bed may include pivots attached to terminal ends of the pillars that are received by the adjustable fasteners. In one embodiment, the threaded cylinders of the adjustable fasteners are rotated to adjust a positioning of the pivots, and the shape of the supporting surface of the bed.

In one embodiment, the bed is a flexible bed and the support surface is a flexible support surface. The bed may be made of carbon fiber or other suitable material. However, in other embodiments, the support surface of the bed may be rigid or semi-rigid. The profile shape of the support surface may be flat, semi-circular, triangular, crescent, or other shape. In certain embodiments, the support surface is made of a radio-transparent material or other suitable material.

In one embodiment of the bed, the frame includes a front frame and a rear frame. Further, a front support panel may be attached to the front frame and a rear support panel may be attached to the rear frame. In addition, the adjustable fasteners of the bed may be arranged along a width of the front support panel and the rear support panel. The front support panel and the rear support panel may include at least one anchor for securing and adjusting supporting ropes. In another embodiment, the front support panel and the rear support panel include at least one shaft hole providing a passage for supporting the supporting ropes.

In yet another embodiment, the bed includes a height adjustment control disposed on the front support panel and the rear support panel for adjusting a height of the bed. The height adjustment control may be disposed at other locations along the bed. A fastener control knob also may be disposed on the frame to fasten the adjustable fasteners to the frame in one embodiment.

At least some embodiments concern a device useful in the medical/veterinary sphere to obtain images of at least a portion of the internal anatomy of a patient, and then perform analyses, diagnoses or other assessments of the patient.

Other features and advantages will become apparent from the following detailed description, taken in conjunction with the accompanying drawings, which illustrate by way of example, the features of the various embodiments.

BRIEF DESCRIPTION OF THE DRAWING

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 37 illustrates a front view of the support panel of a support panel, according to one embodiment;

FIG. 38 illustrates a side view of the support panel of FIG. 37;

FIG. 39 illustrates a top view of the support panel of FIG. 37;

FIG. 41 illustrates a step of adjusting the position of the bed with the adjustable pillar fasteners based on a laser-generated visual marker projected on the patient.

Figure 1:
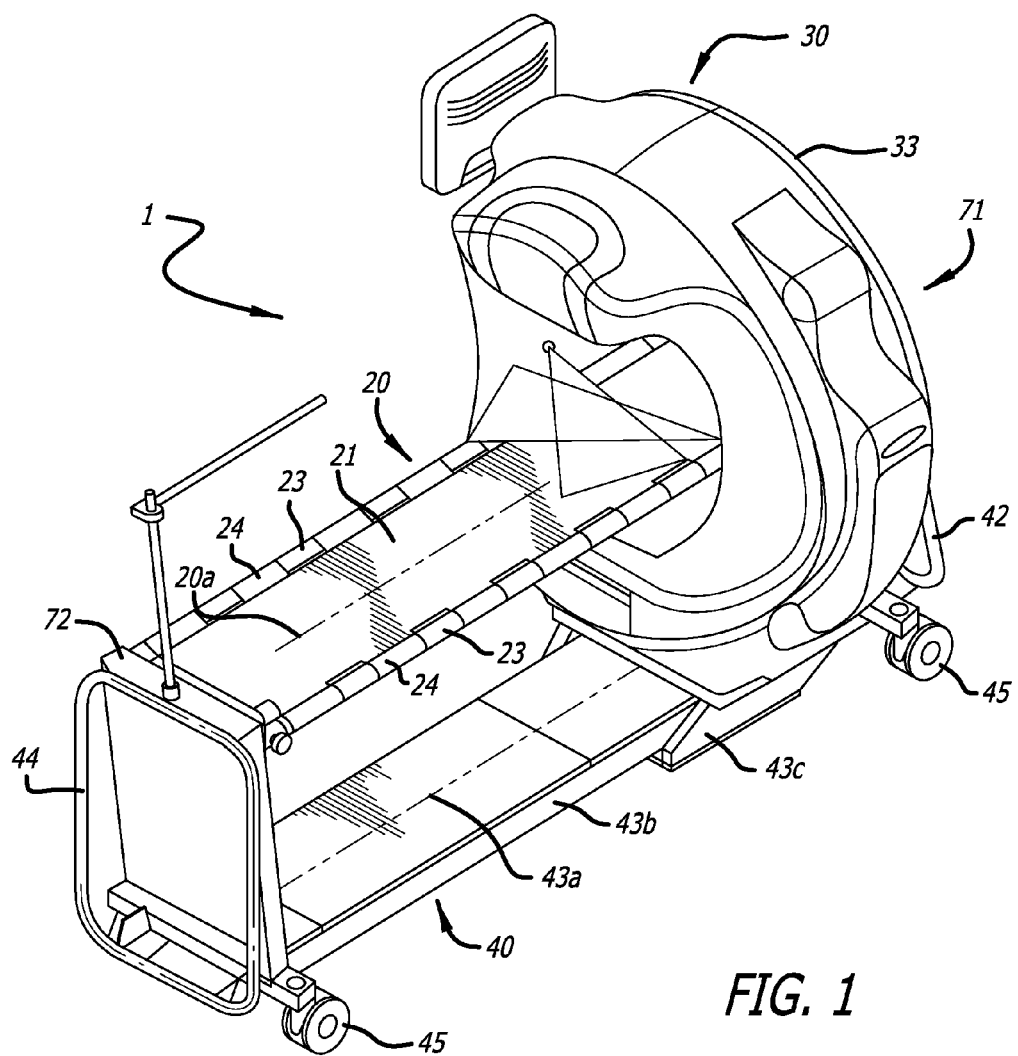
FIG. 1 illustrates an exemplary radiological imaging system, according to one embodiment.

Different ones of the Figures may have at least some reference numerals that are the same in order to identify the same components, although a detailed description of each such component may not be provided below with respect to each Figure.

DETAILED DESCRIPTION

Each of the features and teachings disclosed herein can be utilized separately or in conjunction with other features and teachings to provide a radiological imaging system with a bed. Representative examples utilizing many of these additional features and teachings, both separately and in combination are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that these specific details are not required to practice the teachings of the present disclosure.

Some portions of the detailed descriptions herein are presented in terms of processes and symbolic representations of operations on data bits within a computer memory. These process descriptions and representations are the means used by those skilled in the data processing arts to most effectively convey the substance of their work to others skilled in the art. A process is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. The steps are not intended to be performed in a specific sequential manner unless specifically designated as such.

The methods or processes presented herein are not inherently related to any particular computer or other apparatus. Various general-purpose systems, computer servers, or personal computers may be used with programs in accordance with the teachings herein, or it may prove convenient to construct a more specialized apparatus to perform the method steps. The structure for a variety of these systems will appear from the description below. It will be appreciated that a variety of programming languages may be used to implement the teachings of the disclosure as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples.

According to one embodiment, the present radiological imaging system is useful in both the medical and veterinary applications for performing radiological imaging of at least one portion of the internal anatomy of a patient. In particular, the radiological imaging system is useful for performing X-rays, CT scans, fluoroscopy and other radiological imaging examinations.

FIG. 1 illustrates an exemplary radiological imaging system, according to one embodiment. The radiological imaging system 1 includes a gantry 30, a bed 20, a load-bearing structure 40, and a control unit. The radiological imaging system 1 is suitable for performing the radiological imaging of at least a portion of the patient.

Figure 2:
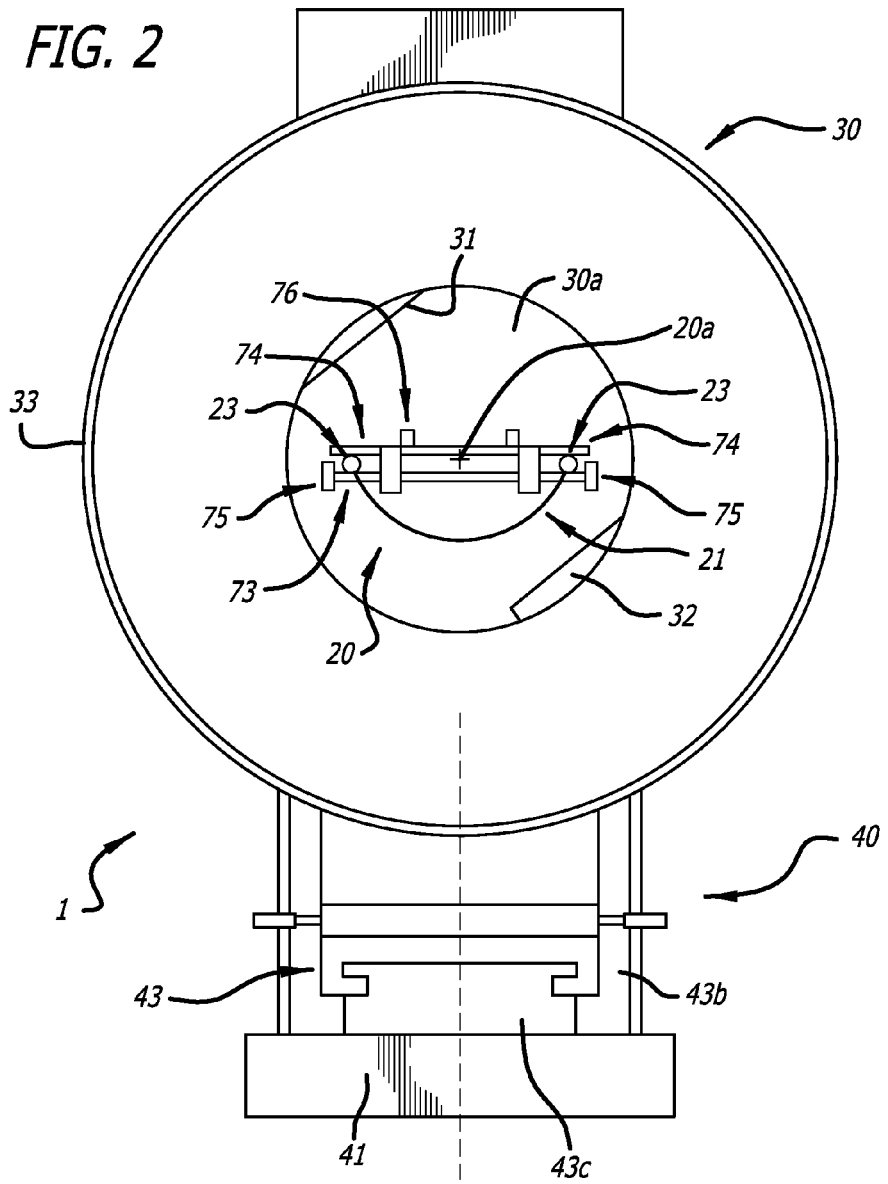
FIG. 2 illustrates a cross-section of the radiological imaging system of FIG. 1.

FIG. 2 illustrates a cross-section of the radiological imaging system of FIG. 1. The gantry 30 has a container that houses various components for performing the radiological imaging. The gantry 30 defines an analysis zone 30a in which at least a portion of the bed 20 extends. The gantry 30 includes a source 31 to emit radiation, such as X-ray, at least one detector 32 to receive the radiation emitted by the source and positioned substantially on the opposite side of the bed 20 from the source; and a housing 33 suitable to contain at least partially the source 31 and the detector 32. In particular, the detector 32 detects the radiation that is emitted from the source 31 and traverses the patient's body. The detector 32 may include a sensing element such as a flat panel detector and/or a linear sensor.

Figure 7:
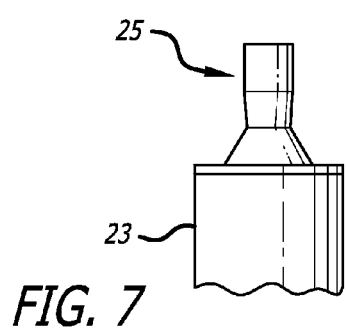
FIG. 7 illustrates a pivot assembly of the radiological imaging system, according to embodiment.

The bed 20 includes a patient support surface 21, two pillars 23 positioned laterally to and on opposite sides of the patient support surface 21, and at least one hook 24 suitable to attach the patient support surface 21 to the two pillars 23, as shown in the embodiments illustrated in FIGS. 3-6. Each end of each pillar 23 includes a pivot 25, as shown in FIG. 7. In one embodiment, the pillars 23 are cylindrically shaped, although this embodiment is not limiting.

Figure 3:
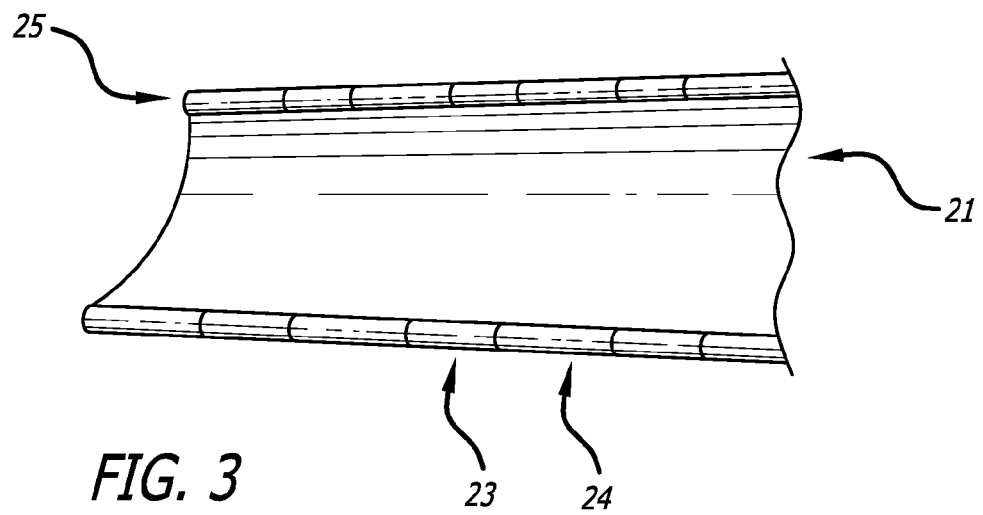
FIG. 3 illustrates a flexible bed of the radiological imaging system, according to one embodiment.
Figure 4:
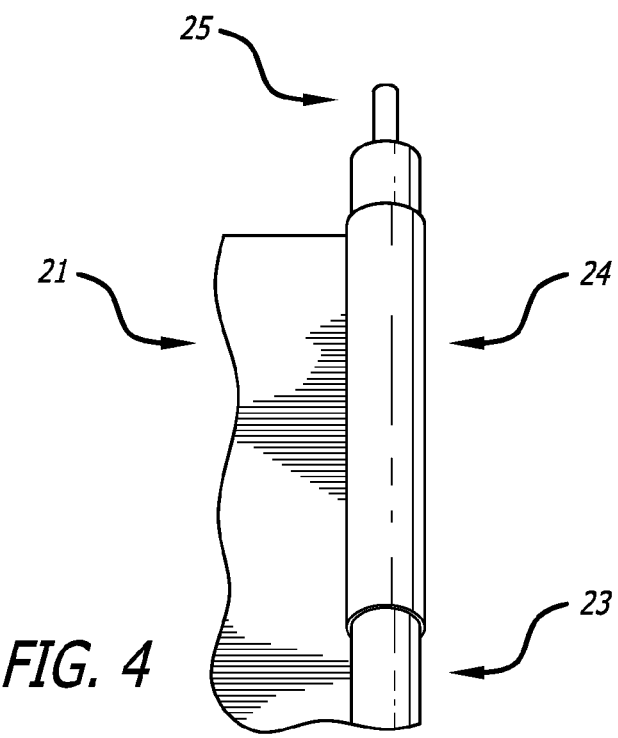
FIG. 4 illustrates a pillar assembly of the flexible bed of FIG. 3.
Figure 5:
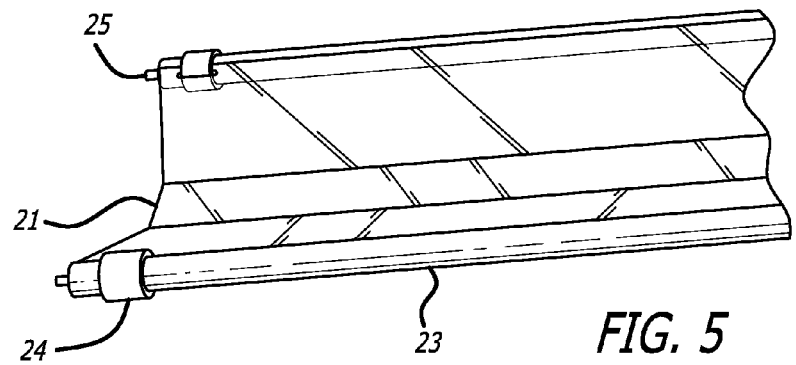
FIG. 5 illustrates a rigid bed of the radiological imaging system, according to another embodiment.
Figure 6:
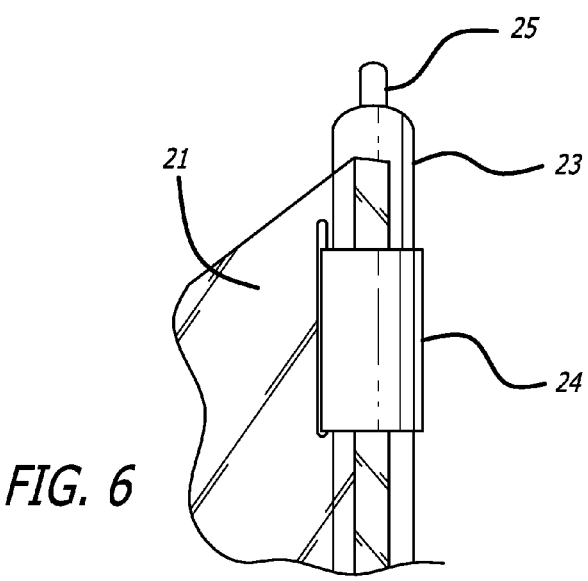
FIG. 6 illustrates a pillar assembly of the rigid bed of FIG. 5.

The bed 20 has a substantially concave support surface to internally house at least a portion of a patient and, in particular, at least the portion to be analyzed portion of the patient. In one embodiment, the patient support surface 21 is flexible, as shown in FIG. 3, and may be constructed from a flexible material, such as, a carbon fiber. In another embodiment, the patient support surface 21 is rigid, as shown in FIG. 5, and may be constructed from a rigid material, such as, for example, poly methyl methacrylate (PMMA) or other plastics. The rigid patient support surface 21 may be constructed in various profile shapes, such as flat, semicircular, curved, and triangular shapes, or other appropriate shapes.

The bed 20, or at least the patient support surface 21, can be made from a radio-transparent material that is transparent to X-rays. Specifically, the patient support surface 21 is made from a material having reduced Hounsfield units.

Figure 8:
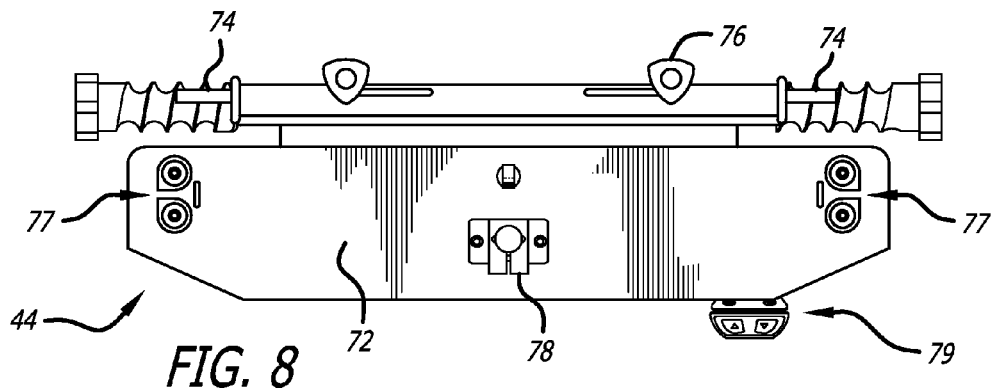
FIG. 8 illustrates a rear support panel of the radiological imaging system, according to one embodiment.
Figure 9:
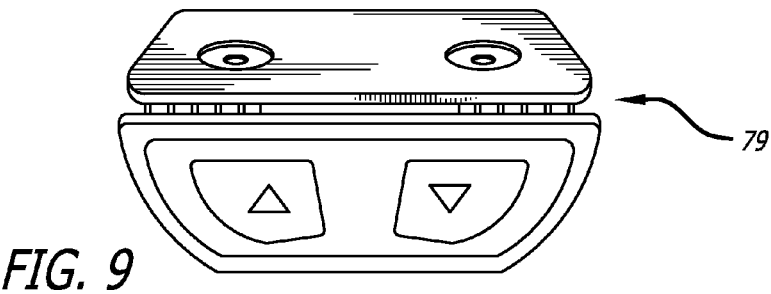
FIG. 9 illustrates a height adjustment control panel of the rear support panel of FIG. 8.
Figure 10:
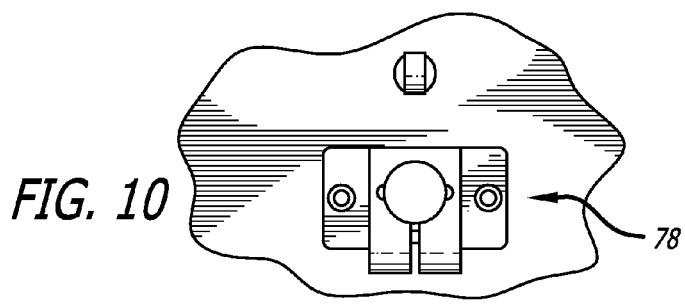
FIG. 10 illustrates a shaft hole of the rear support panel of FIG. 8.
Figure 11:
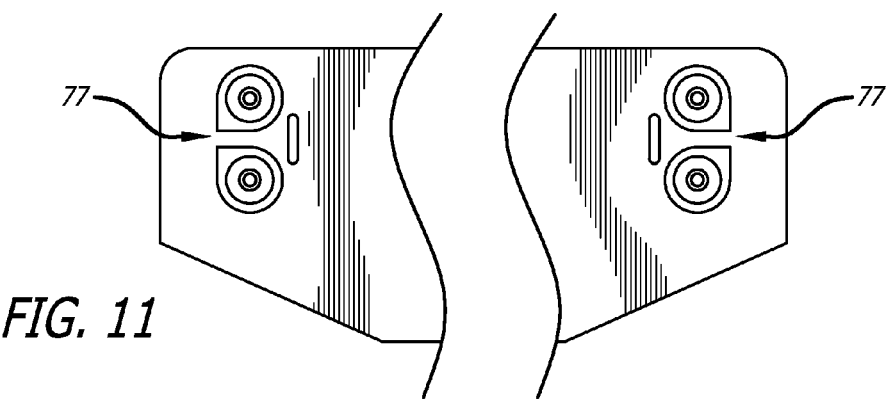
FIG. 11 illustrates anchors of the rear support panel of FIG. 8.
Figure 14:
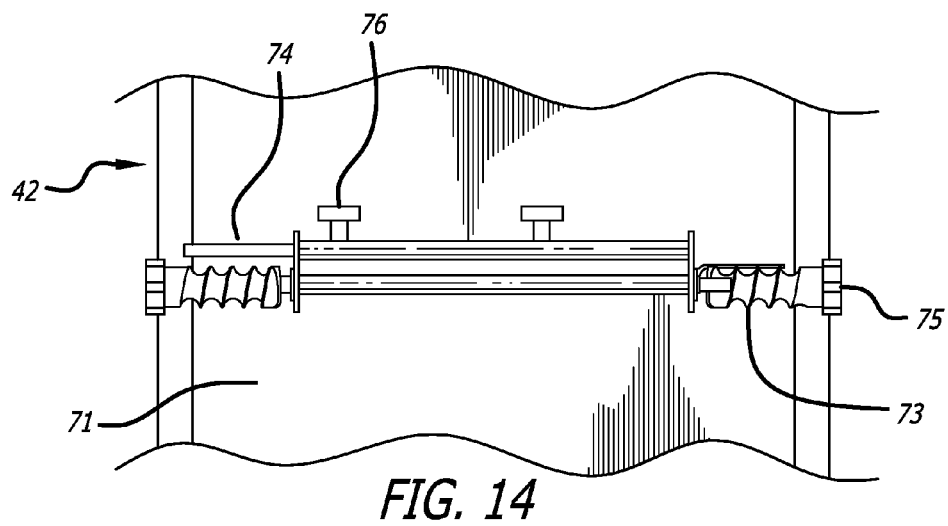
FIG. 14 illustrates a front support panel of the radiological imaging system, according to one embodiment.
Figure 28:
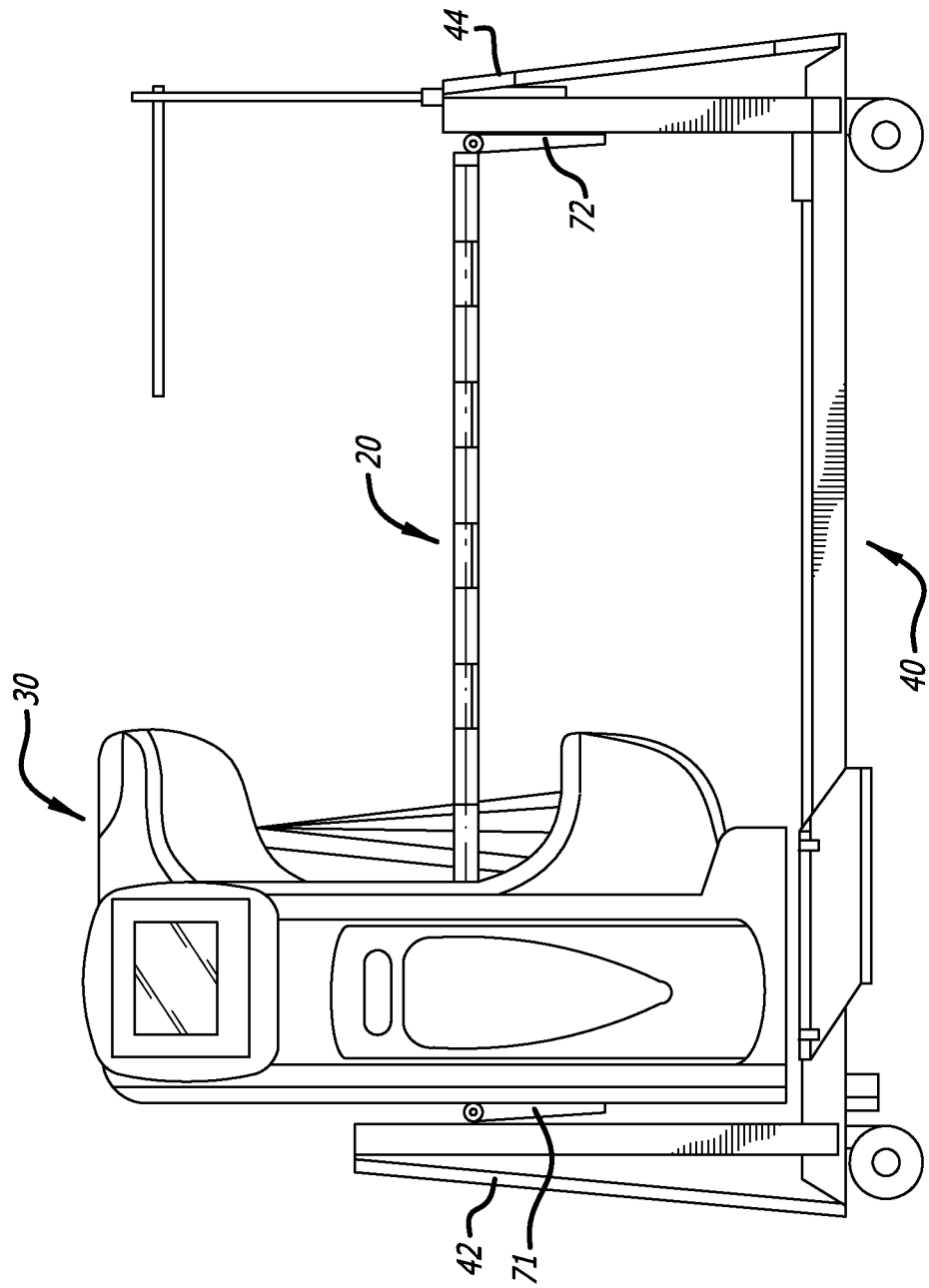
FIG. 28 illustrates a side view of the radiological imaging.

As illustrated in FIG. 1, the load-bearing structure 40 includes a base 41 to support the gantry 30; at least one frame suitable to support the bed 20 in a raised position from the floor 1a; translation mechanism 43 suitable to move the gantry 30 in a sliding direction 43a that extends substantially parallel to the direction of extension 20a; and wheels 45 that may be pivoting (or not) and are suitable to rest on the floor 1a to enable movement of the radiological imaging system 1. In one embodiment, the load-bearing structure 40 includes two frames, a front frame 42 positioned at a front end of the load-bearing structure 40 and a rear frame 44 positioned at a rear end of the load-bearing structure, where the front and rear ends are in the opposite sides along the direction 20a. Additionally, a front support panel 71 is attached to the front frame 42, as shown in FIG. 14, and a rear support panel 72 is attached to the rear frame 44, as shown in FIG. 8. In FIG. 1, a rear support panel 72 is attached to the rear frame 44. The front support panel 71 can be attached similarly to the front frame 42, as shown in FIG. 28. The panels 71 and 72 can be attached to other parts of the respective frames 42 and 44, besides as discussed above. In another embodiment, the load-bearing structure 40 shown in FIG. 1 may include a rotation device (not shown) suitable to rotate the gantry about an axis of rotation that is substantially perpendicular to the direction of extension 20a and, specifically, substantially perpendicular to the floor 1a.

The translation mechanism 43 includes a linear guide 43b suitable to control the translation along the sliding direction 43a substantially parallel to the direction 20a and a carriage 43c suitable to slide along the linear guide 43b. In one embodiment, the linear guide 43b is motorized. Additionally, the translation of the gantry 30 in the sliding direction 43a can be controlled by the control unit.

The front support panel 71 shown in FIG. 14 and the rear support panel 72 shown in FIG. 8 further include adjustable pillar fasteners 73 and locks 74. In one embodiment, the adjustable pillar fasteners 73 and locks 74 are arranged along the width of the front support panel 71 and the rear support panel 72, as shown in FIGS. 14 and 8, respectively. In particular, a pair comprising one adjustable pillar fastener 73 and one lock 74 is positioned at each of a left side of the front support panel 71, a right side of the front support panel 71, a left side of the rear support panel 72, and a right side of the rear support panel 72.

Figure 12:
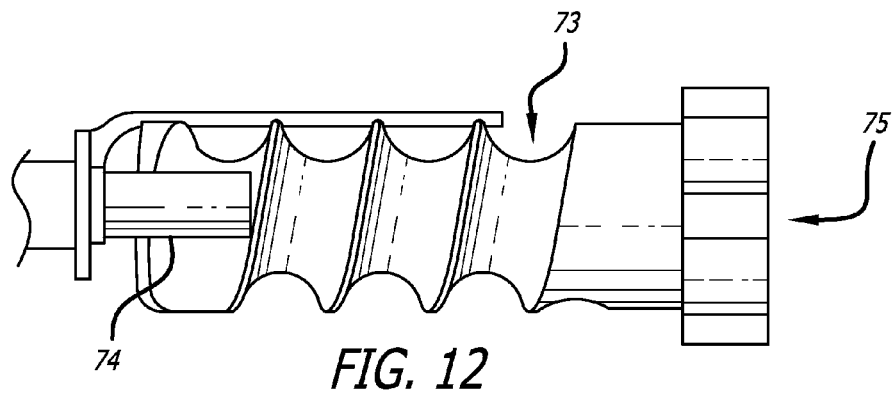
FIG. 12 illustrates an adjustable pillar fastener and a lock in a disengaged position, according to one embodiment.
Figure 13:
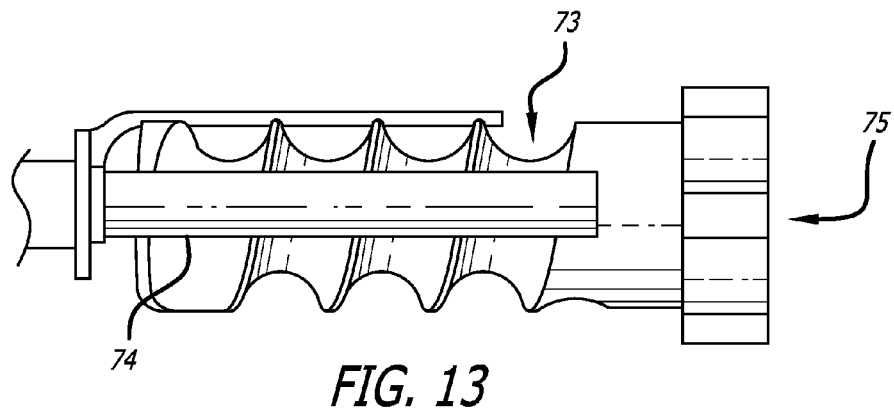
FIG. 13 illustrates the adjustable pillar fastener and the lock of FIG. 12 in an engaged position.

The adjustable pillar fasteners 73 and locks 74 are described with reference to FIGS. 12-14. In one embodiment, the adjustable pillar fasteners 73 are externally threaded cylinders (i.e., screw-shaped). The adjustable pillar fasteners 73 are adapted to receive the pivots 25. More particularly, the pivots 25 rest in a root of the threading of the adjustable pillar fasteners 73 such that the axis of a pivot 25 is substantially perpendicular to the axis of the adjustable pillar fastener 73. In some embodiments, the axis of the pivot 25 may form an angle with the axis of the adjustable pillar fastener 73. When the adjustable pillar fasteners 73 are rotated, the resulting screw action of the threading causes the pivots 25 to translate left or right, depending on the direction of rotation. In one embodiment, fastener control knobs 75 are provided on the adjustable pillar fasteners 73 for rotating the adjustable pillar fasteners 73. In one embodiment, the adjustable pillar fasteners 73 may be rotated by a motor, a motorized mechanism, or by hand.

According to one embodiment, the locks 74 are stainless steel rods positioned in parallel with the adjustable pillar fasteners 73. Each lock 74 may further include a lock control knob 76, which may be, in some embodiments, a spring-loaded mechanism or a handle, for engaging and disengaging the lock 74. When the locks 74 are in a disengaged position (FIG. 12), the threads of the adjustable pillar fasteners 73 are exposed, and the pivots 25 may be placed on the adjustable pillar fasteners 73. In an engaged position (FIG. 13), the locks 74 extend to cover at least the threaded portion of the adjustable pillar fasteners 73. Thus, by virtue of engaging the locks 74, the pivots 25 are secured between the adjustable pillar fasteners 73 and the locks 74.

In another embodiment, the front support panel 71 and/or the rear support panel 72 include(s) one or more additional components. Referring to FIGS. 8-11, the additional components include one or more of the followings: one or more anchors 77, one or more shaft holes 78, and a height adjustment control panel 79. The anchors 77 allow for securing and adjusting supporting ropes (not shown) for immobilizing a part or whole of the patient, for example, a limb of a veterinary patient. The shaft holes 78 provide a passage for supporting ropes or for intravenous feeding tubes (not shown). The height adjustment control panel 79 controls a height adjustment mechanism (not shown), for example, independent pistons mounted inside the front support panel 71 and/or the rear support panel 72, to raise or lower the bed 20.

In another embodiment, the above-mentioned additional components of the support panels 71 and/or 72, including, without limitation, the adjustable pillar fasteners 73, the locks 74, the fastener control knobs 75, the lock control knobs 76, the anchors 77, the shaft holes 78, and the height adjustment control panel 79, are provided directly on the front and/or rear frames 42, 44.

According to one embodiment, the radiological imaging system 1 adjusts the patient positioning in the following steps. First, with reference to FIG. 1, the gantry 30 is moved to a suitable position on the linear guide 43b to allow access to the load-bearing structure 40. In one embodiment, an operator controls the translation of the gantry 30 by a control unit, as described above. Additionally, each lock 74 is disengaged (e.g., the locks 74 in FIGS. 8 and 14).

Figure 22:
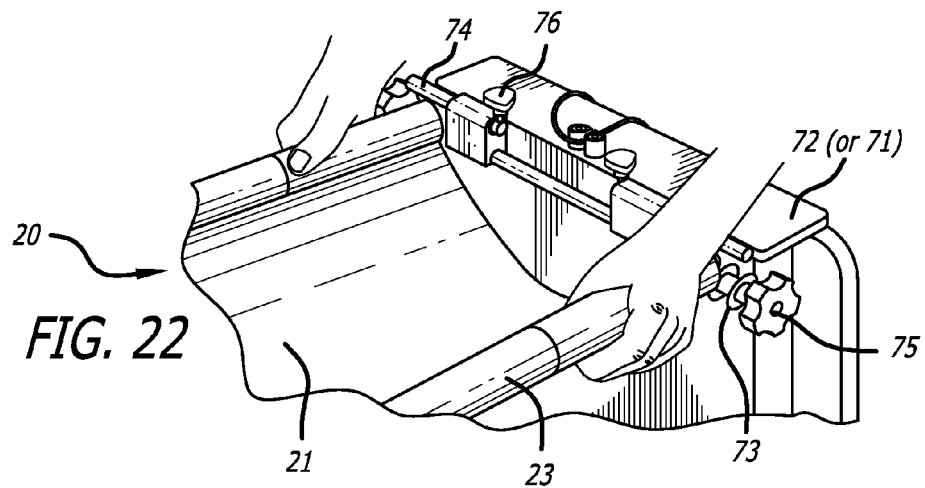
FIG. 22 illustrates a step of placing the bed on a load-bearing structure of the radiological imaging system.
Figure 23:
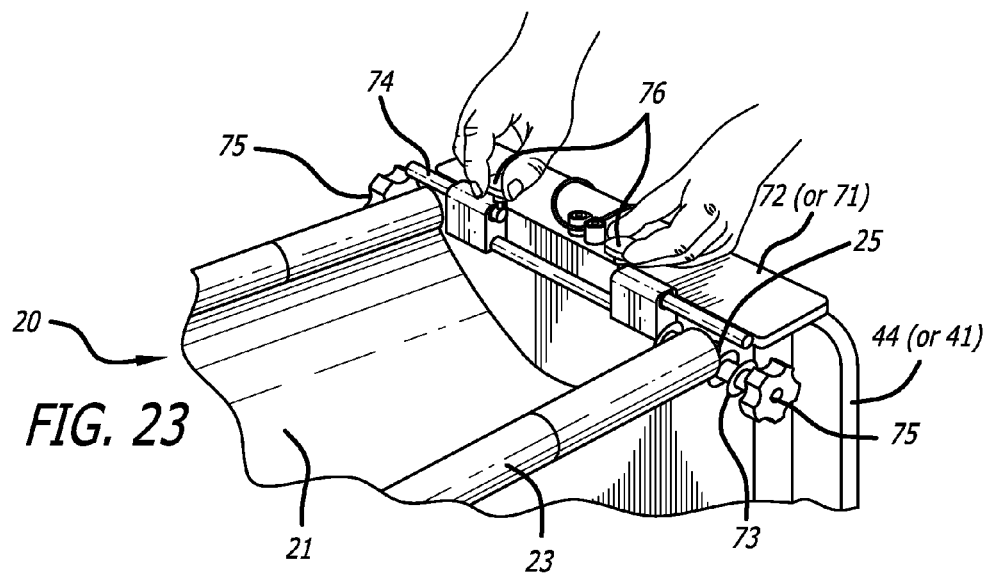
FIG. 23 illustrates a step of engaging the locks of the radiological imaging system.

After the gantry 30 is moved, the bed 20 is inserted into the gantry 30 as shown in FIG. 22 (gantry 30 not shown in FIG. 22), and the pivots 25 are placed on corresponding ones of the adjustable pillar fasteners 73 of the rear support panel 72. Similarly, the pivots 25 on the opposite end of the bed 20 are also placed on corresponding ones of the adjustable pillar fasteners 73 of the front support panel 71. Once the pivots 25 have been placed, the locks 74 are engaged using the lock control knobs 76 to secure the pivots 25 between the adjustable pillar fasteners 73 and the locks 74, as shown in FIG. 23.

Figure 24:
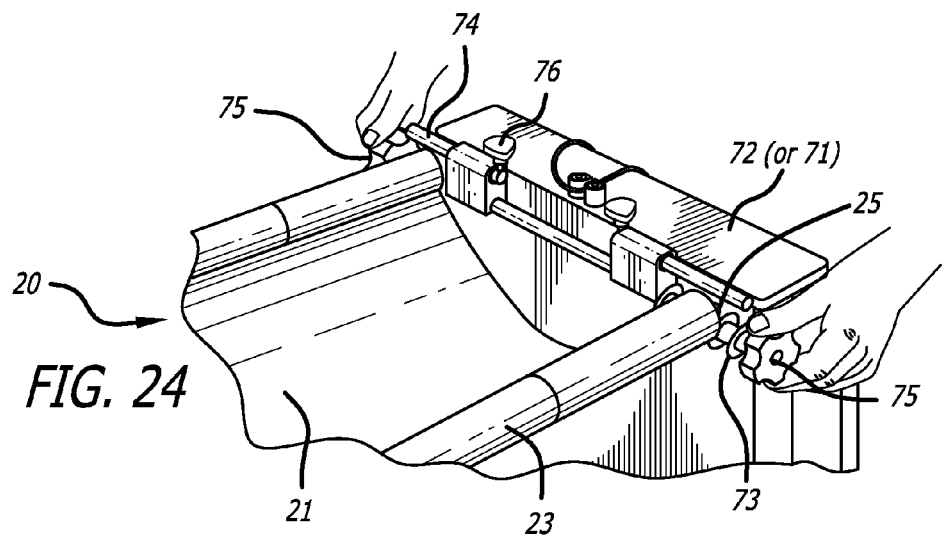
FIG. 24 illustrates a step of adjusting the positioning of the bed of the radiological imaging system.

The width and position of the patient support surface 21 of bed 20 are adjusted by rotating the adjustable pillar fasteners 73, for example, by turning the fastener control knobs 75, to translate the pivots 25 left or right, as shown in FIG. 24. Each adjustable pillar fastener 73, and thus each pivot 25, is independently adjustable. By adjusting the pivots 25, the position of the pillars 23, and thus the shape of the patient support surface 21, can be adjusted.

Figure 15:
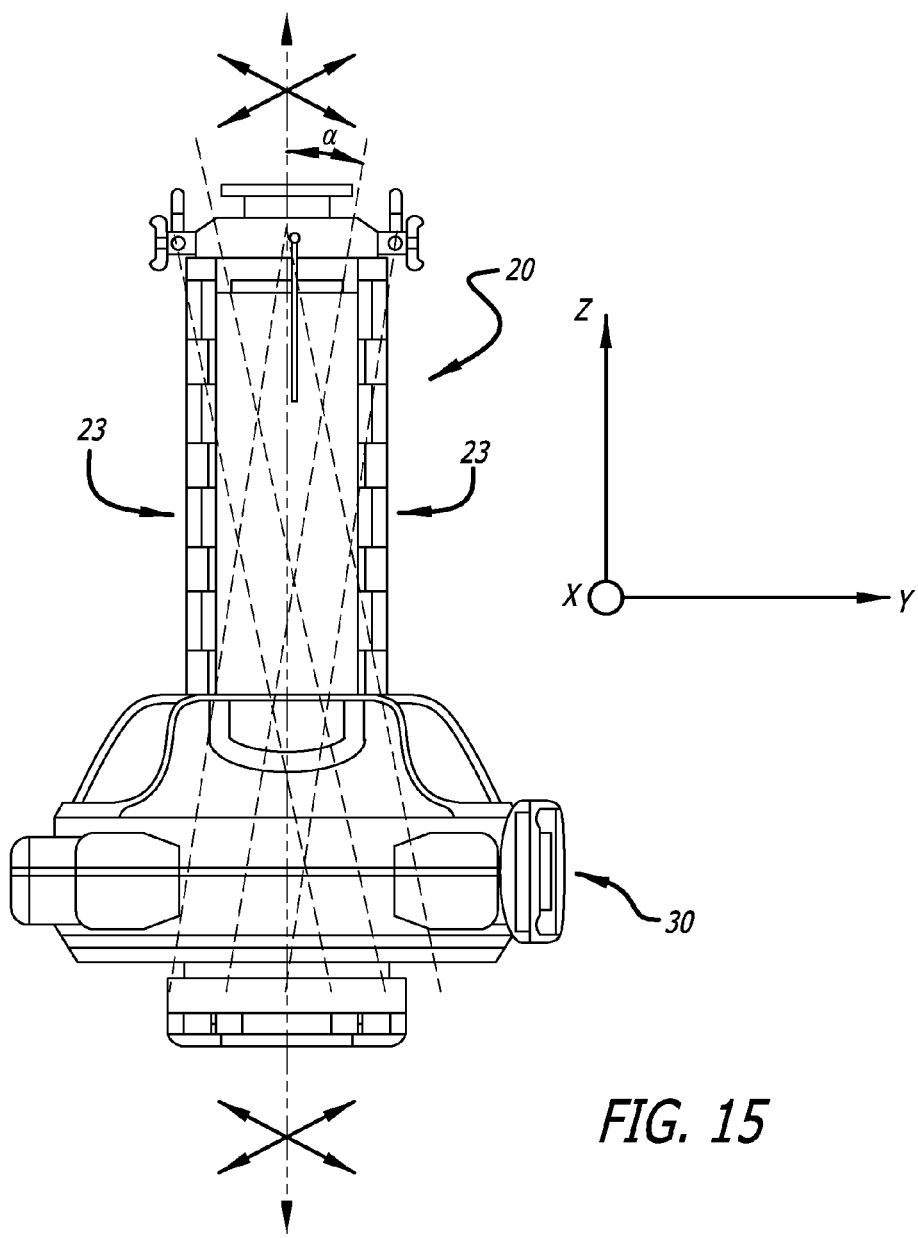
FIG. 15 illustrates angular adjustment of the bed of the radiological imaging system, according to one embodiment.

For example, the angle of each pillar 23 can be adjusted within the gantry 30. Accordingly, an angle $\alpha$ of the bed 20 can be adjusted relative to a z-axis, as illustrated in FIG. 15 (in one embodiment, the z-axis corresponds to the direction 20a of FIG. 1), for example, up to 30° away from the z-axis, although this example is not limiting.

Figure 16:
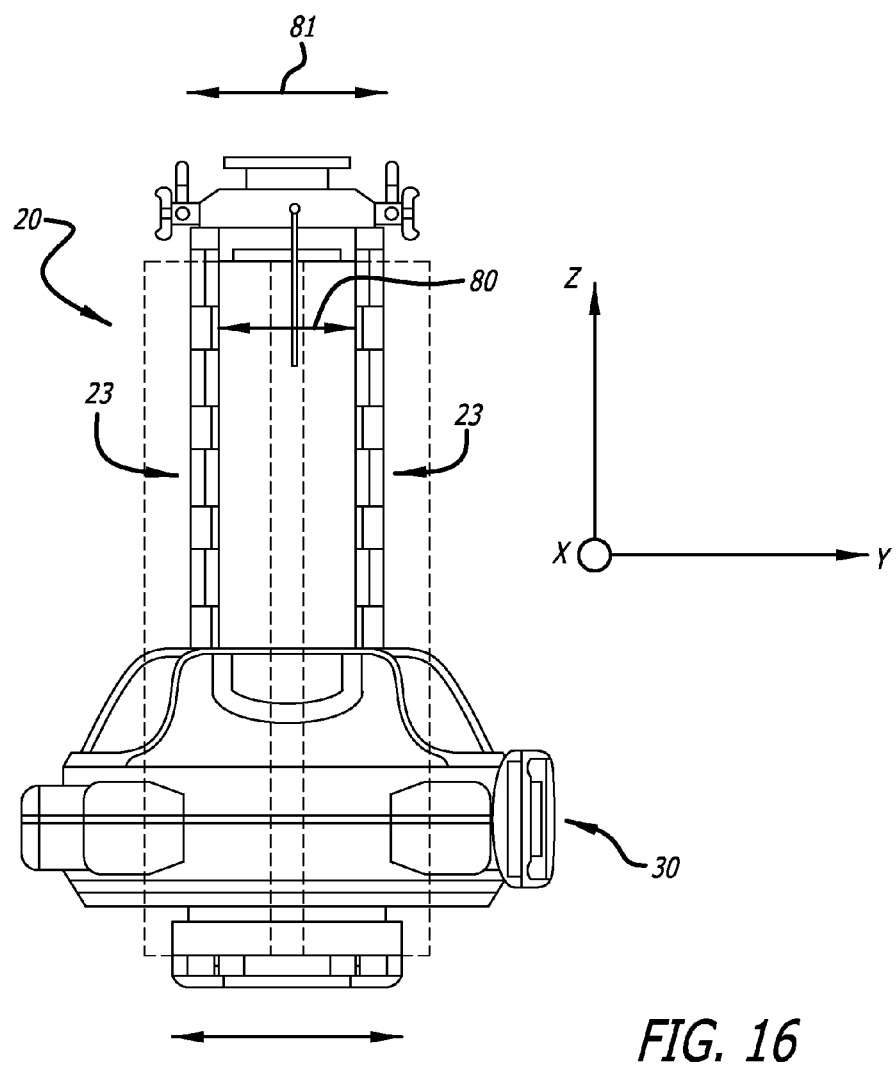
FIG. 16 illustrates width and lateral adjustment of the bed of the radiological imaging system, according to an one embodiment.
Figure 29:
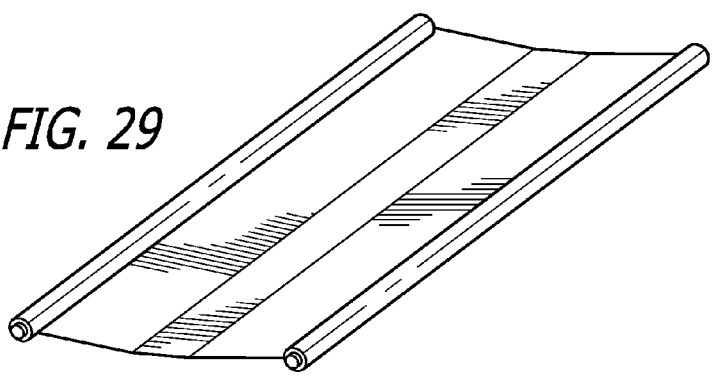
FIG. 29 illustrates a flexible bed of the radiological imaging system, according to one embodiment.
Figure 30:
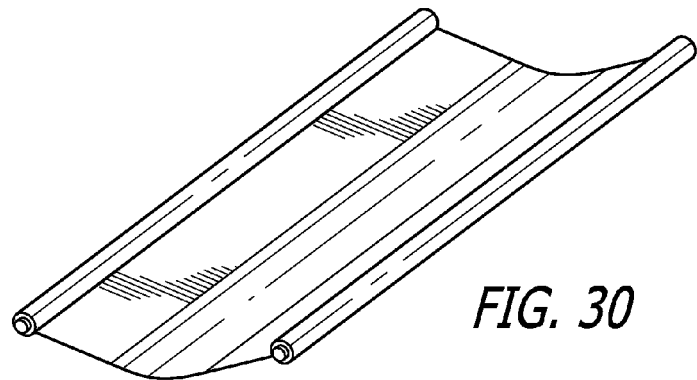
FIG. 30 illustrates the flexible bed of FIG. 29, where the flexible bed is adjusted to a narrower, deeper, and more concave configuration.
Figure 31:
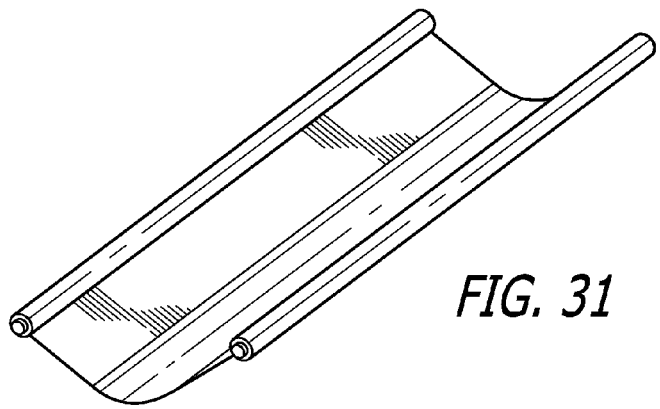
FIG. 31 illustrates the flexible bed of FIG. 30, where the flexible bed is adjusted to a narrower, deeper, and more concave configuration.
Figure 32:
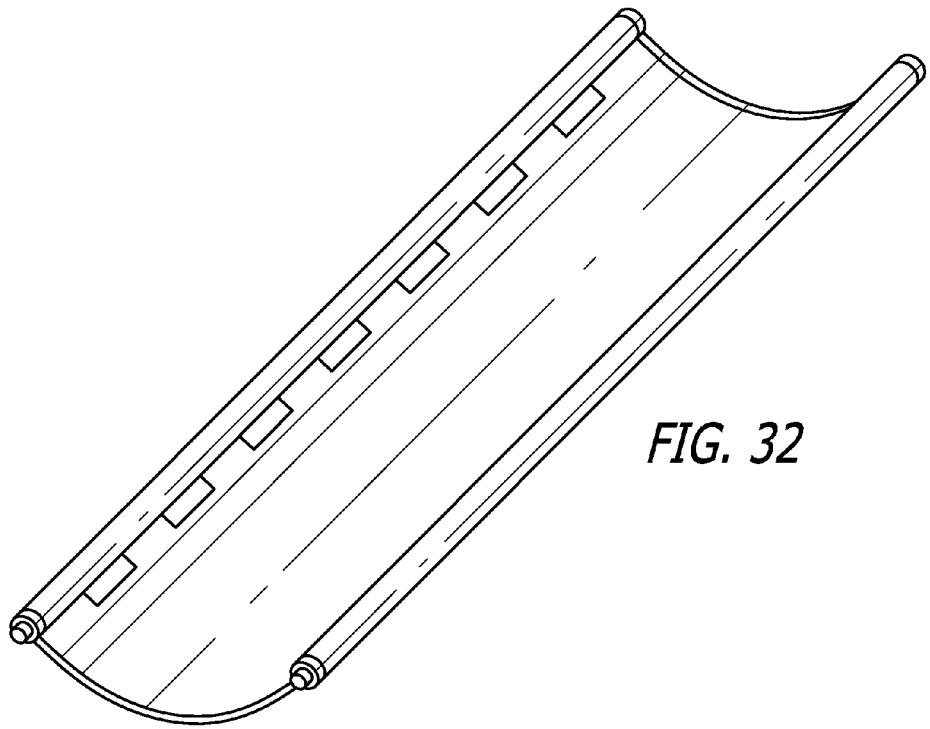
FIG. 32 illustrates a flexible bed of the radiological imaging system, according to one embodiment, where the bed is in a concave configuration.
Figure 33:
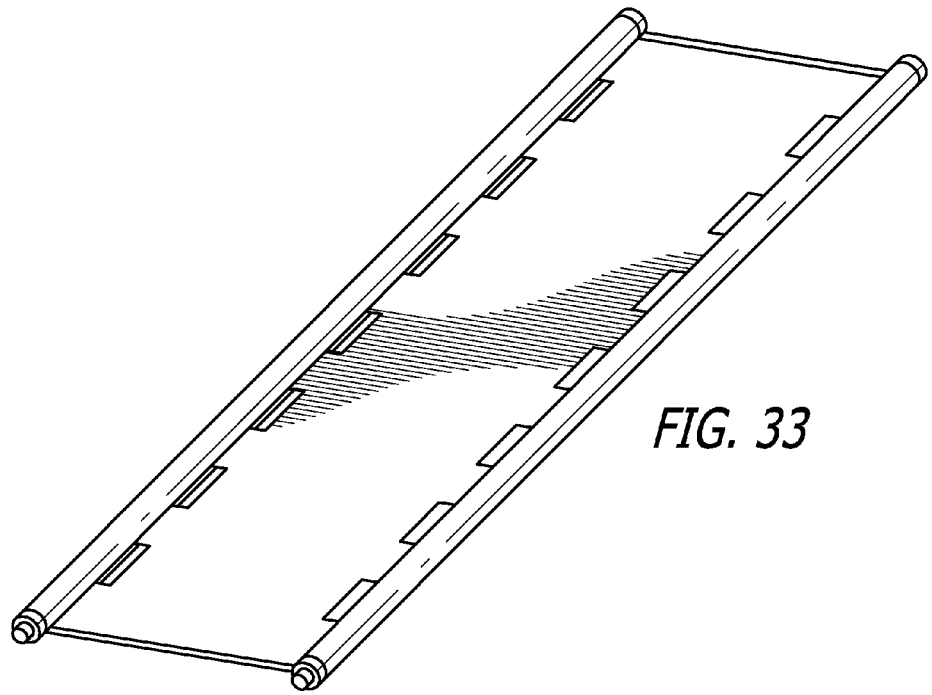
FIG. 33 illustrates a flexible bed of the radiological imaging system, according to one embodiment, where the bed is in a flat configuration.
Figure 34:
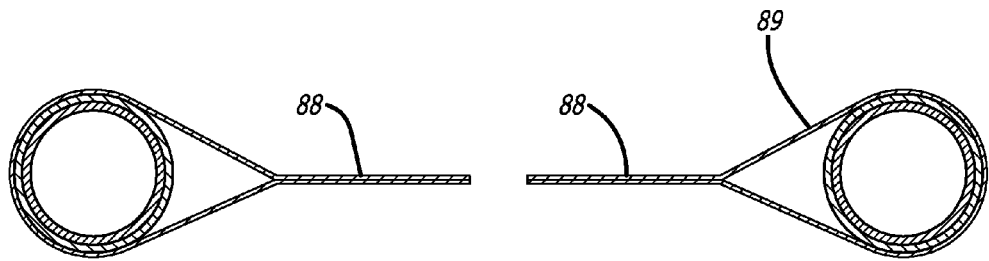
FIG. 34 illustrates a front view of the flexible bed, according to one embodiment.

Additionally, as illustrated in FIG. 16, the width 80 and lateral position 81 of the bed 20 can be adjusted by rotating the adjustable pillar fasteners 73 (not shown in FIG. 16) to move the two pillars 23 away from or towards each other while maintaining a parallel relation between the two pillars 23. Furthermore, the depth and concavity of the flexible patient support surface 21 of the bed 20 are adjustable, as they are related to the width 80, and thus also can be adjusted to be wider or narrower, and more or less concave, by rotating the adjustable pillar fasteners 73. For example, when the pillars 23 are moved away from each other, the bed 20 becomes wider, shallower, and less concave. On the other hand, when the pillars 23 are moved towards each other, the bed 20 becomes narrower, deeper, and more concave. An example of progression of a width, depth, and concavity adjustment of a bed 20 is illustrated in FIGS. 29, 30, and 31. By virtue of adjusting the width, depth, and concavity of the flexible patient support surface 21 of the bed 20, the bed 20 may be configured to be concave, as illustrated, for example, in FIG. 32 or flat, as illustrated, for example, in FIG. 33, although these examples are not limiting. FIG. 34 illustrates a front view of the flexible bed showing the overlapping area for sewing 88 and the seal 89. The seal 89 may be made with a fabric, for example, CORDURA fabric.

Figure 17:
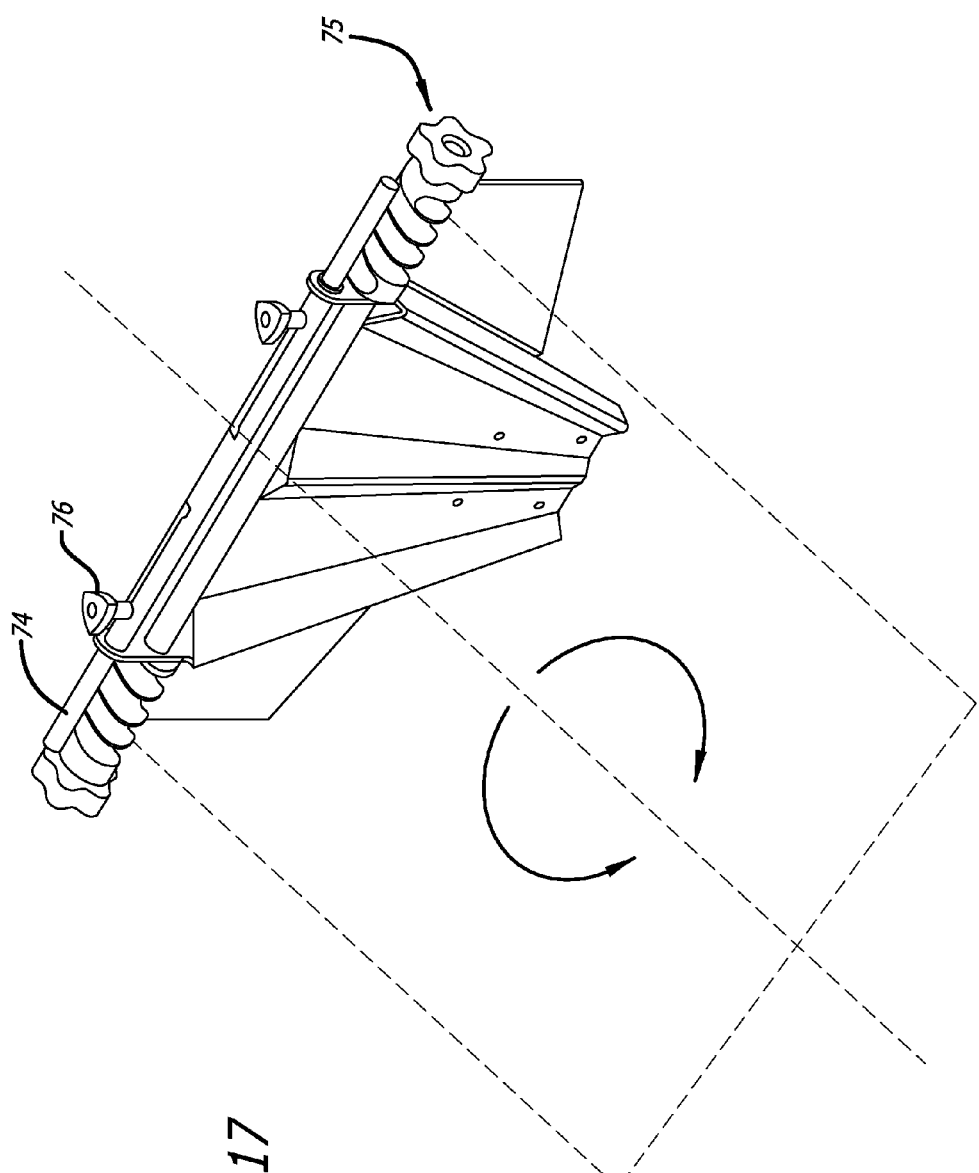
FIG. 17 illustrates adjustment of the inclination of the bed of the radiological imaging system around an axis corresponding to a direction of extension, according to one embodiment.
Figure 18:
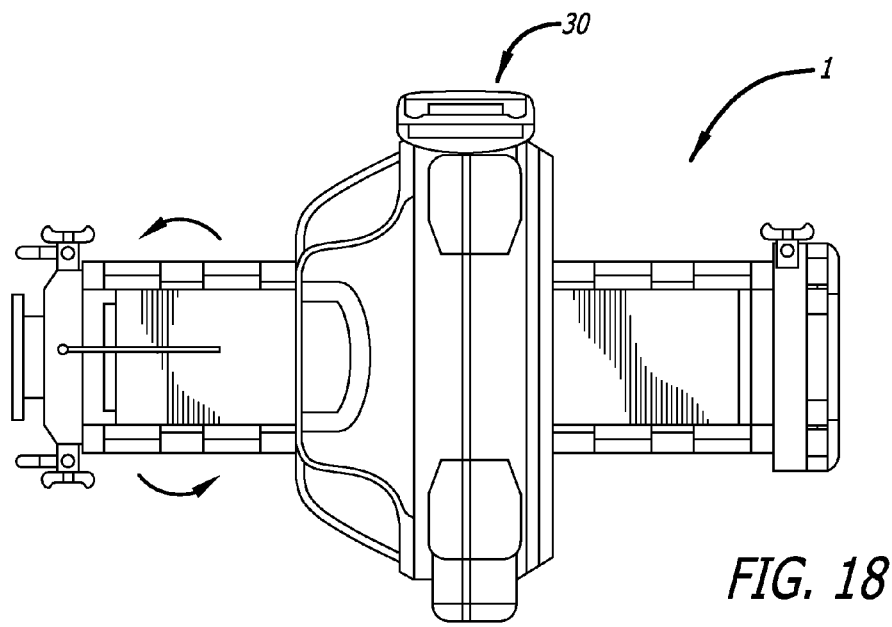
FIG. 18 illustrates adjustment of the inclination of the bed of the radiological imaging system around an axis corresponding to a direction of extension, according to another embodiment.
Figure 19:
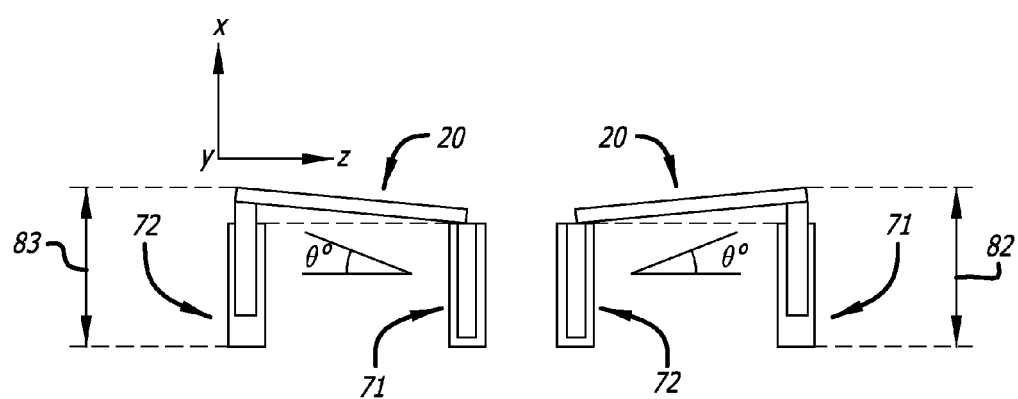
FIG. 19 illustrates height adjustment of the bed of the radiological imaging system, according to one embodiment.
Figure 27:
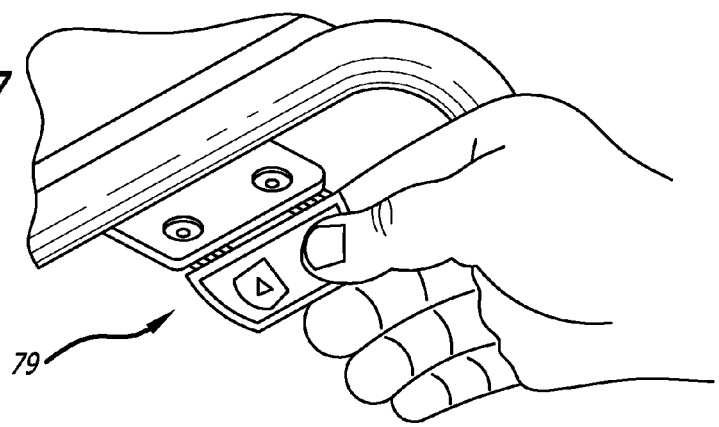
FIG. 27 illustrates a step of adjusting the height of the bed of the radiological imaging system.

Furthermore, as illustrated in FIGS. 17 and 18, an inclination of the bed 20 around an axis substantially parallel to the direction of extension 20a may be adjusted. Moreover, the height adjustment control panel 79 can be operated, as shown in FIG. 27, to adjust the height 82 of the bed 20 at the front support panel 71 and/or the height 83 of the bed 20 at the rear support panel 72, and to adjust an angle of inclination θ, as illustrated in FIG. 19. The angle of inclination of the patient is adjusted inside the gantry. In one embodiment, the adjustable pillar fasteners 73 can be rotated to bring each of the two pillars 23 within close proximity of each other to form a cage from the flexible patient support surface 21.

Figure 25:
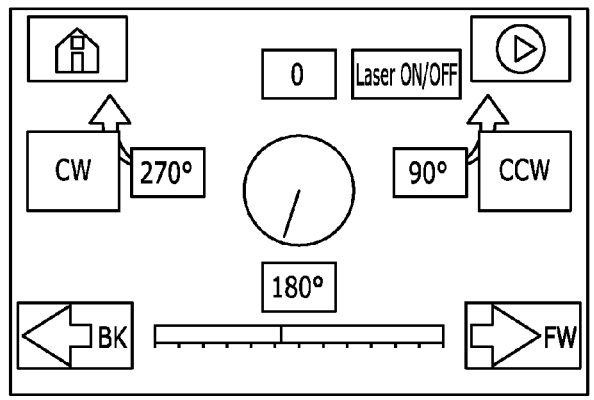
FIG. 25 illustrates a step of activating a laser centering system.
Figure 26:
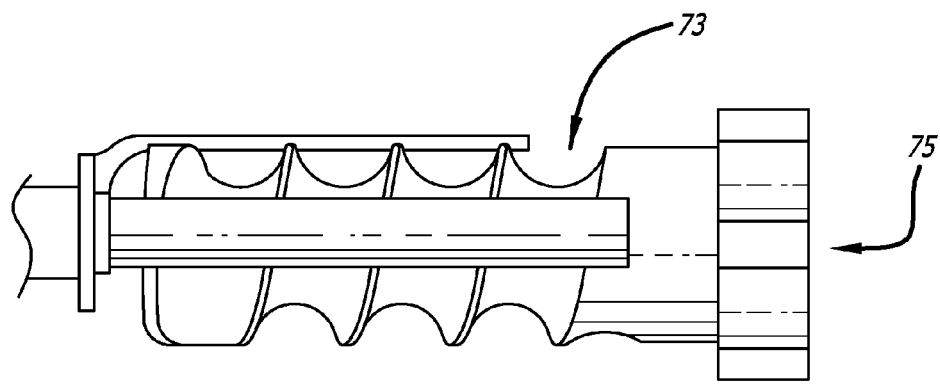
FIG. 26 illustrates an adjustable pillar fastener and a lock in an engaged position, according to one embodiment.
Figure 40:
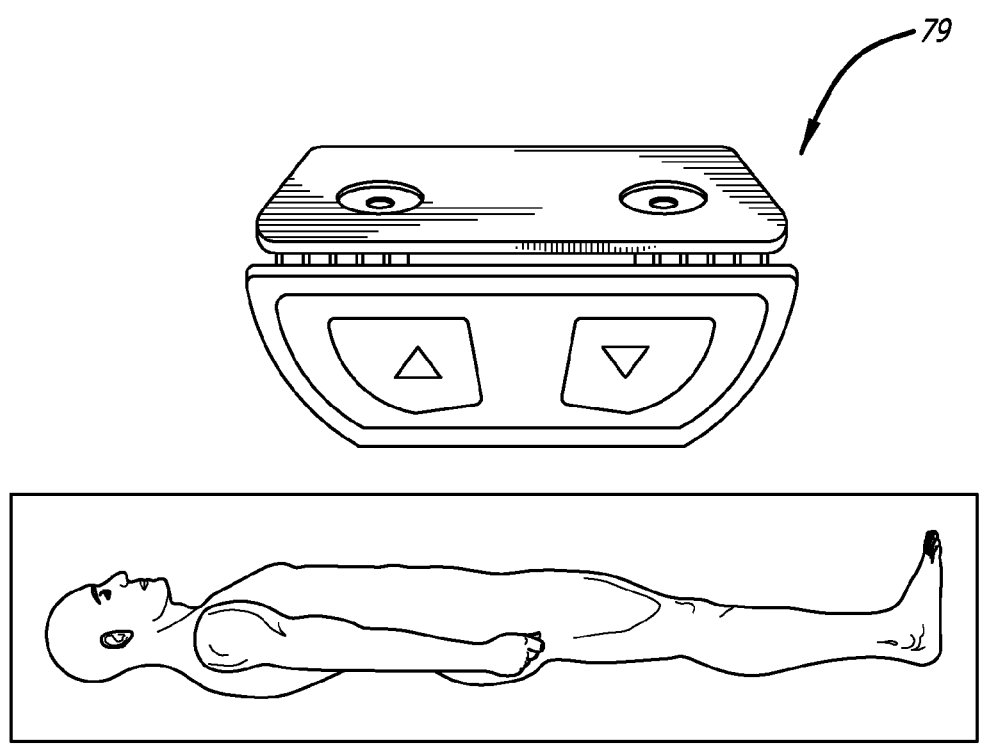
FIG. 40 illustrates a step of adjusting the height of the bed based on a laser-generated visual marker projected on the patient.

In view of the foregoing, it will become apparent to persons skilled in the relevant art(s) that multiple degrees of freedom are available for arranging the bed 20 in various positions and arrangements. Once the bed 20 has been positioned as desired, the patient is placed on the bed 20 and one or more imaging operations are performed. During an imaging operation, the position of the patient may be adjusted as necessary without removing the patient from the bed 20 by adjusting the adjustable pillar fasteners 73 by, for example, rotating the fastener control knobs 75 illustrated in FIG. 26, and by adjusting the bed 20 height using height adjustment control panel 79 illustrated in FIG. 27. In one embodiment, a laser centering system may be activated on a control panel, illustrated in FIG. 25, to project a visual marker to facilitate patient positioning, as illustrated in FIGS. 40 and 41. The height and the position of the patient can be adjusted by the height adjustment control panel 79 and/or the fastener control knobs 75 to position the visual marker on an area of interest on the patient to achieve a desired alignment for imaging.

Figure 35:
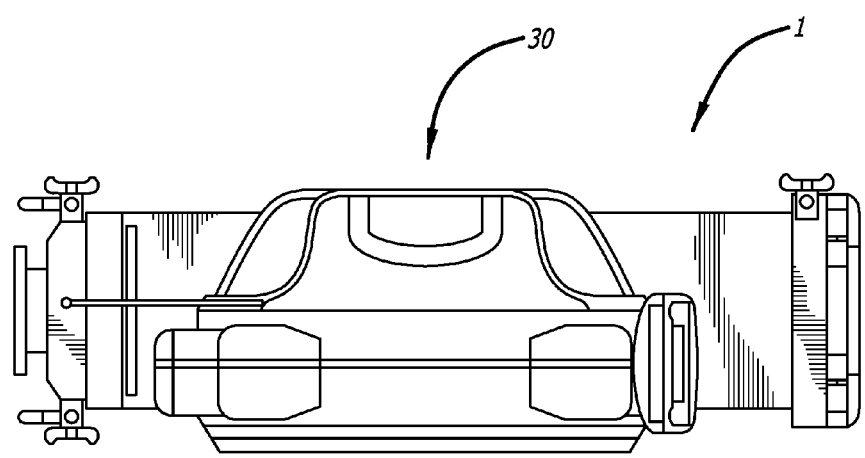
FIG. 35 illustrates a top view of a radiological imaging system, where a gantry is rotated into a position for transport or storage.
Figure 36:
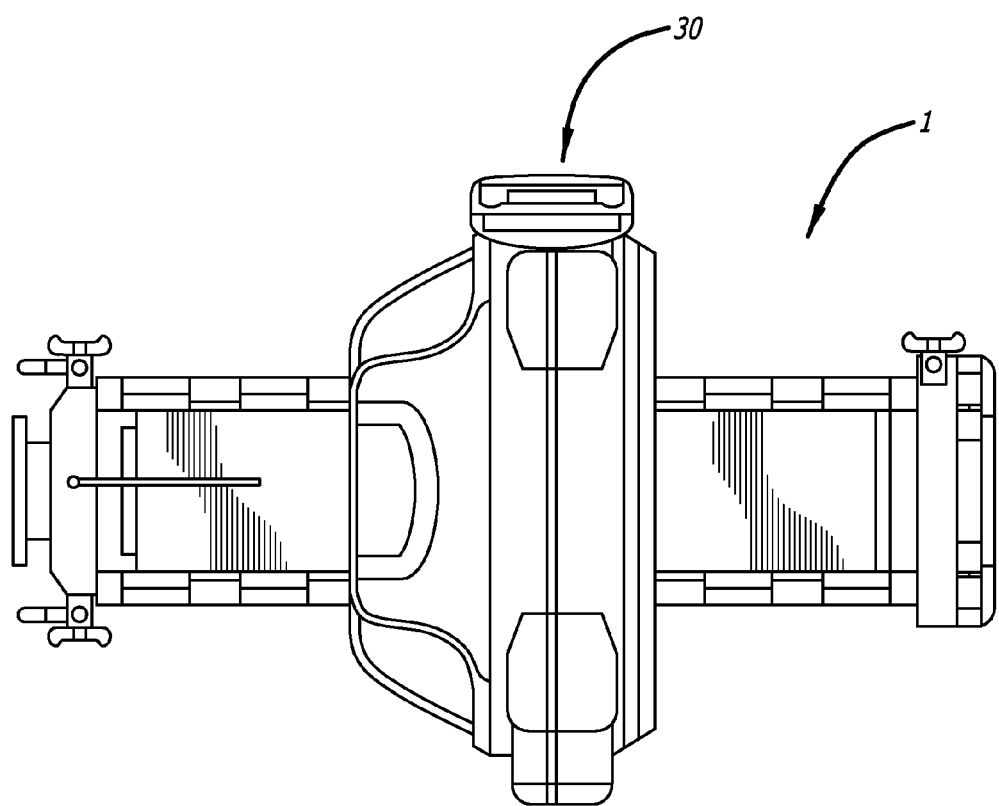
FIG. 36 illustrates a top view of a radiological imaging system of FIG. 35, where the gantry is rotated into a position for imaging.

After the imaging operation is complete, the patient is removed from the bed 20. Further, the bed 20 may be removed, for storage or transport purposes, for example, by disengaging the locks 74 and removing the bed 20 from the load-bearing structure 40. Then, the gantry 30 may be rotated into a position for storage or transport as illustrated in FIG. 35. FIG. 36 illustrates a top view of a radiological imaging system, where the gantry is rotated into a position for imaging.

According to one embodiment, the radiological imaging system 1 including the bed 20 is easily adjustable to arrange a patient supported in the bed 20 in an optimal position for and during imaging and/or other medical or veterinary procedures. For example, veterinary patient diseases, such as lordosis and kyphosis, may cause misalignments of the patient or a portion of the patient relative to the radiological imaging system 1 (and in particular, relative to the source 31 and the detector 32), resulting in imaging errors. By virtue of the adjustable bed 20, the position and inclination of the patient can be adjusted and aligned relative to the source 31 and the detector 32 of the radiological imaging system 1. According to one embodiment, the adjustable bed 20 adjusts its size to adapt the patient size and keep the patient in place.

Figure 20:
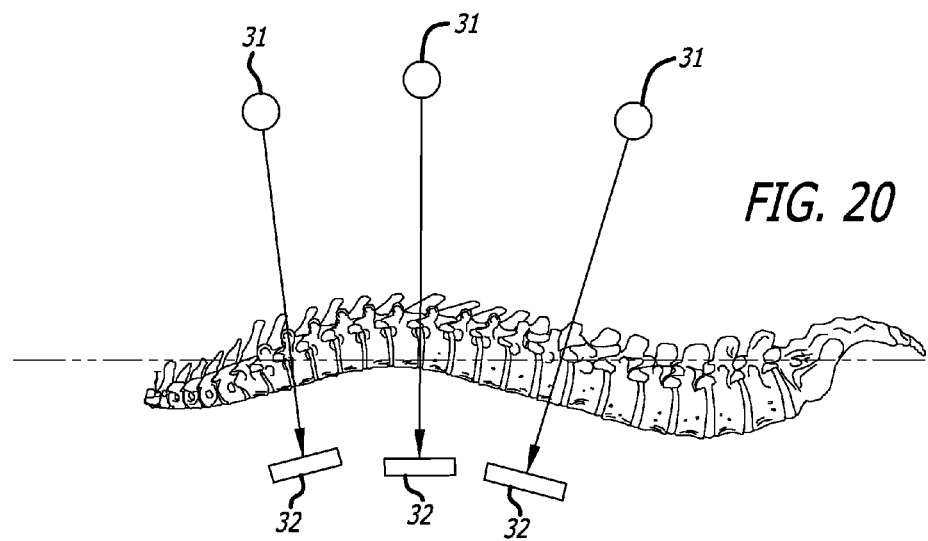
FIG. 20 illustrates imaging geometries for an example veterinary patient.
Figure 21:
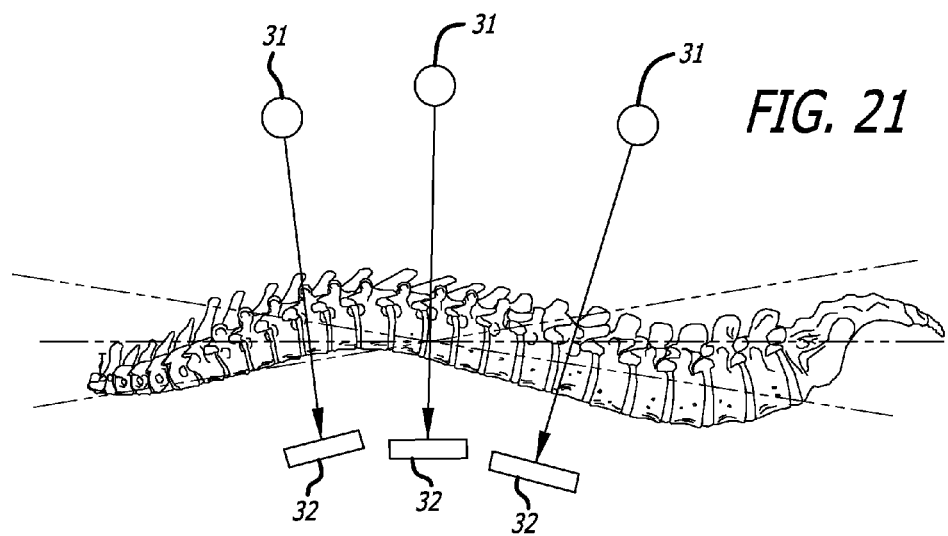
FIG. 21 illustrates imaging geometries for an example veterinary patient, where inclination of the patient is adjusted by adjusting the bed of the radiological imaging system, according to one embodiment.

FIG. 37 illustrates a front view of a support panel, according to one embodiment. The support panel may be a front support panel 71 or a rear support panel 72. FIGS. 38 and 39 illustrate a side view and a top view of the support panel. FIG. 17 illustrates adjustment of the inclination of the bed of the radiological imaging system 1 around an axis of rotation that corresponds to a direction of extension of the bed. FIG. 18 illustrates a top view of the adjustment of the inclination of the bed of the radiological imaging system 1 around the axis of rotation. FIG. 20 illustrates imaging geometries for an example veterinary patient in a horizontal position. In this example, there are three X-ray sources 31 and three detectors 32. The inclination of the veterinary patient can be adjusted by adjusting the bed of the radiological imaging system 1 as shown in FIG. 21. The alignment capability of the bed reduces the errors generated by the veterinary patient.

Also provided by virtue of the adjustable bed 20, efficiency, e.g., the length of time to complete a procedure, and safety of the patient, as well as the operators, are improved over existing radiological imaging devices. Moreover, the bed 20 may also be removed from the load-bearing structure 40 and gantry 30 to be used as a wheeled stretcher, also referred to as a gurney.

The various embodiments described above have been presented by way of example and not limitation. It will be apparent to persons skilled in the relevant art(s) that various changes in form and detail can be made therein without departing from the spirit and scope of the present disclosure. Thus, the present disclosure should not be limited by any of the above-described exemplary embodiments.

In addition, it should be understood that any attached figures, which highlight functionality described herein, are presented as illustrative examples. The structure of the present radiological imaging system is sufficiently flexible and configurable, such that it can be utilized in ways other than that shown in the drawings.

Further, the purpose of the appended Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present disclosure in any way.

What is claimed:
1. A radiological imaging system comprising:
   a bed including a support surface, pillars extending along an elongational axis of the bed, and pivots attached to terminal ends of the pillars;
   a load-bearing structure having a frame to support the bed;
   adjustable fasteners removably attached to the frame, wherein the adjustable fasters are threaded cylinders;
   wherein the pivots are received by the adjustable fasteners, and wherein the threaded cylinders of the adjustable fasteners are rotated to adjust a positioning of the pivots and the shape of the support surface.

2. The radiological imaging system of claim 1, wherein the bed is a flexible bed, and wherein the support surface is a flexible support surface.

3. The radiological imaging system of claim 2, wherein the flexible bed is made of carbon fiber.

4. The radiological imaging system of claim 1, wherein the support surface is a rigid surface having a flat, semicircular, curved, or triangular profile shape.

5. The radiological imaging system of claim 1, wherein the support surface is made of a radio-transparent material.

6. The radiological imaging system 1, wherein the frame comprises a front frame and a rear frame.

7. The radiological imaging system of claim 6, further comprising a front support panel attached to the front frame and a rear support panel attached to the rear frame.

8. The radiological imaging system of claim 7, wherein the adjustable fasteners are arranged along a width of the front support panel and the rear support panel.

9. The radiological imaging system of claim 7, wherein the front support panel and the rear support panel include at least one anchor for securing and adjusting supporting ropes.

10. The radiological imaging system of claim 9, wherein the front support panel and the rear support panel include at least one shaft hole providing a passage for supporting the supporting ropes.

11. The radiological imaging system of claim 9, further comprising a height adjustment control disposed on the front support panel and the rear support panel for adjusting a height of the bed.

12. The radiological imaging system of claim 1, further comprising a fastener control knob disposed on the frame to fasten the adjustable fasteners to the frame.

13. The radiological imaging system of claim 1, further comprising a gantry and a translation mechanism to move the gantry in a sliding direction that extends along the elongational axis of the bed.

14. The radiological imaging system of claim 13, wherein the translation mechanism includes a linear guide and a carriage that control a translational position of the gantry with respect to the bed.

15. The radiological imaging system of claim 14, wherein the linear guide is motorized.

16. The radiological imaging system of claim 1, further comprising a lock suitable to secure the pivots to the adjustable fasteners.

17. The radiological imaging system of claim 16, wherein the lock is a spring-loaded lock.

18. The radiological imaging system of claim 16, wherein threaded cylinders of the adjustable fasteners are exposed when the lock is in a disengaged position.

19. The radiological imaging system of claim 16, wherein the lock extends a portion of the threaded cylinders in an engaged position.

20. The radiological imaging system of claim 1, further comprising a laser centering system, wherein the laser centering system projects a visual marker on a patient placed on the bed.

21. The radiological imaging system of claim 1, further comprising a source suitable to emit radiation, and a detector suitable to receive the radiation that traversed a portion of a patient positioned on the bed.

22. A bed for use with a radiological imaging system, the bed comprising:
a frame;
pillars extending along an elongational axis of the bed and connected to the frame;
a support surface connected to the pillars;
adjustable fasteners removably attached to the frame, wherein the adjustable fasteners are threaded cylinders; and
pivots attached to terminal ends of the pillars that are received by the adjustable fasteners;
wherein the threaded cylinders of the adjustable fasteners are rotated to adjust a positioning of the pivots, and the shape of the supporting surface.

23. The bed of claim 22, wherein the bed is a flexible bed, and wherein the support surface is a flexible support surface.

24. The bed of claim 22, wherein the flexible bed is made of carbon fiber.

25. The bed of claim 22, wherein the support surface is a rigid surface having a flat, semicircular, curved or triangular profile shape.

26. The bed of claim 22, wherein the support surface is made of a radio-transparent material.

27. The bed of claim 22, wherein the frame includes a front frame and a rear frame.

28. The bed of claim 27, further comprising a front support panel attached to the front frame and a rear support panel attached to the rear frame.

29. The bed of claim 28, wherein the adjustable fasteners are arranged along a width of the front support panel and the rear support panel.

30. The bed of claim 28, wherein the front support panel and the rear support panel include at least one anchor for securing and adjusting supporting ropes.

31. The bed of claim 30, wherein the front support panel and the rear support panel include at least one shaft hole providing a passage for supporting the supporting ropes.

32. The bed of claim 30, further comprising a height adjustment control disposed on the front support panel and the rear support panel for adjusting a height of the bed.

33. The bed of claim 22, further comprising a fastener control knob disposed on the frame to fasten the adjustable fasteners to the frame.

* * * * *